US006812378B2

(12) United States Patent
Banno et al.

(10) Patent No.: US 6,812,378 B2
(45) Date of Patent: Nov. 2, 2004

(54) ESR1—A PLANT GENE THAT CAN PROMOTE PLANT REGENERATION AND TRANSFORMATION

(75) Inventors: Hiroharu Banno, New York, NY (US); Nam-Hai Chua, Scarsdale, NY (US)

(73) Assignee: The Rockefeller University, New York, NY (US)

( * ) Notice: Subject to any disclaimer, the term of this patent is extended or adjusted under 35 U.S.C. 154(b) by 40 days.

(21) Appl. No.: 10/102,949

(22) Filed: Mar. 22, 2002

(65) Prior Publication Data

US 2002/0157140 A1 Oct. 24, 2002

Related U.S. Application Data

(62) Division of application No. 09/604,394, filed on Jun. 27, 2000, now Pat. No. 6,407,312.

(51) Int. Cl.[7] .......................... C12N 15/82; C12N 5/11; C12N 15/74; A01H 5/00

(52) U.S. Cl. ....................... 800/278; 800/290; 800/298; 800/306; 536/23.1; 435/320.1

(58) Field of Search .......................... 800/278; 536/23.8

(56) References Cited

PUBLICATIONS

Aoyama, T. et al. "A glucocorticoid–mediated transcriptional induction system in transgenic plants", *The Plant Journal*, 1997; 11(3):605–612.

Barry, G.F. et al. "Identification of a cloned cytokinin biosynthetic gene", *Proc. Natl. Acad. Sci. USA*, Aug. 1984; 81:4776–4780.

Chuck, G. et al. "KNAT1 Induces Lobed Leaves with Ectopic Meristems When Overexpressed in Arabidopsis", *The Plant Cell*, Aug. 1996; 8:1277–1289.

Ebinuma, H. et al. "Selection of marker–free transgenic plants using the isopentenyl transferase gene", *Proc. Natl. Acad. Sci. USA*, Mar. 1997; 94:2117–2121.

Faiss, M. et al. "Conditional transgenic expression of the ipt gene indicates a function for cytokinins in paracrine signaling in whole tobacco plants", *The Plant Journal*, 1997; 12(2):401–415.

Kakimoto, T. "CKI1, a Histidine Kinase Homolog Implicated in Cytokinin Signal Transduction", *Science*, Nov. 8, 1996; 274:982–985.

Lincoln, C. et al. "A knotted1–like Homeobox Gene in Arabidopsis is Expressed in the Vegetative Meristem and Dramatically Alters Leaf Morphology When Overexpressed in Transgenic Plants", *The Plant Cell*, Dec. 1994; 6:1859–1876.

Ohme–Takagi, M. et al. "Ethylene–Inducible DNA Binding Proteins That Interact with an Ethylene–Responsive Element", *The Plant Cell*, Feb. 1995; 7:173–182.

Ooms, G. et al. From tumour to tuber; tumour cell characteristics and chromosome numbers of crown gall–derived tetraploid potato plants (*Solanum tuberosum* cv. 'Maris Bard'), *Theor. Appl. Genet.*, 1983; 66:169–172.

Riou–Khamlichi, C. et al. "Cytokinin Activation of Arabidopsis Cell Division Through a D–Type Cyclin", *Science*, Mar. 5, 1999; 283:1541–1544.

Smigocki, A.C. et al. "Cytokinin gene fused with a strong promoter enhances shoot organogenesis and zeatin levels in transformed plant cells", *Proc. Natl. Acad. Sci. USA*, Jul. 1988; 85:5131–5135.

Smigocki, A.C. et al. "Cytokinin–to–Auxin Ratios and Morphology of Shoots and Tissues Transformed by a Chimeric Isopentenyl Transferase Gene", *Plant Physiol.*, 1989; 91:808–811.

Zuo, J. et al. "Chemical–inducible systems for regulated expression of plant genes", *Current Opinion in Biotechnology*, 2000; 11:146–151.

GenBank Accession No. AC007357; Vysotskaia, V.S. et al., "*Arabidopsis thaliana* chromosome 1 BAC F3F19 sequence".

GenBank Accession No. D38124; Ohme–Takagi, M.

*Primary Examiner*—Elizabeth F. McElwain
*Assistant Examiner*—Georgia Helmer
(74) *Attorney, Agent, or Firm*—Rothwell Figg Ernst & Manbeck

(57) ABSTRACT

A plant gene, Esr 1, has been found which when overexpressed in plant cells results in cells which have cytokinin-independent cell growth. This feature allows the encoded protein ESR1 to be used as a selectable marker of transformed cells by growing the transformed cells on cytokinin-free media. It has also been found that overexpression of ESR1 in cells grown in the presence of cytokinins results in a higher regeneration of plants. This feature allows the gene to be used to obtain greater regeneration of plant cells.

5 Claims, No Drawings

ESR1— A PLANT GENE THAT CAN PROMOTE PLANT REGENERATION AND TRANSFORMATION

CROSS REFERENCE TO RELATED APPLICATIONS

This application is a divisional of Ser. No. 09/604,394, filed Jun. 27, 2000 now U.S. Pat. No. 6,407,312.

BACKGROUND OF THE INVENTION

Organogenesis in tissue culture is a critical step for efficient transformation of most plants. Media of controlled auxin/cytokinin ratio govern organogenesis in a wide range of species. Cytokinins were first identified as factors that act synergistically with auxin to promote cell division and act antagonistically to auxin to promote shoot and root initiation from callus cultures. Cytokinins have been implicated in many aspects of plant growth and development, including cell division, shoot initiation and growth, leaf senescence, and photomorphogenesis. Although most molecular mechanisms of cytokinin action are unknown, overexpression of a histidine kinase CKI1 or cyclin D3 confers cytokinin-independent cell growth on cultured cells of *Arabidopsis* (Kakimoto, 1996; Riou-Kharnlichi et al., 1999), indicating that they may play key roles in cytokinin-signaling.

Transgenic techniques have become a powerful tool to address important biological problems in multicellular organisms, and this is particularly true in the plant field. Many approaches that were impossible to implement by traditional genetics can now be realized by transgenic techniques, including the introduction into plants of homologous or heterologous genes, with modified functions and altered expression patterns. The success of such techniques often depends upon the use of markers to identify the transgenic plants and promoters to control the expression of the transgenes.

Selectable markers are widely used in plant transformation. Historically such markers have often been dominant genes encoding either antibiotic or herbicide resistance (Yoder and Goldsbtrough; 1994). Although such markers are highly useful, they do have some drawbacks. The antibiotics and herbicides used to select for the transformed cells generally have negative effects on proliferation and differentiation and may retard differentiation of adventitious shoots during the transformation process (Ebinuma et al., 1997). Also, some plant species are insensitive to or tolerant of these selective agents, and therefore, it is difficult to separate the transformed and untransformed cells or tissues (Ebinuma et al., 1997). Further, these genes are constitutively expressed, and there are environmental and health concerns over inserting such constitutively expressed genes into plants which are grown outside of a laboratory setting (Bryant and Leather, 1992; Gressel, 1992; Flavell et al., 1992).

One marker which is neither an antibiotic nor a herbicide is the ipt gene. This gene encodes isopentenyltransferase which is used in cytokinin synthesis (Barry et al., 1984). Overproduction of cytokinins results in the overproduction of shoots (Barry et al., 1984). This overproduction of shoots can result in a phenotype having a large number of shoots (hereafter "shooty phenotype"). This phenotype can be used as a marker (Ebinuma et al., 1997). A chimeric ipt-gene under the control of the cauliflower mosaic virus (CaMV) promoter has been introduced into cells of potato (Ooms et al., 1983), cucumber (Smigocki and Owens, 1989), and several *Nicotiana* species (Smigocki and Owens, 1988) and these transgenic cells proliferated and exhibited an extreme shooty phenotype and loss of apical dominance in hormone-free medium. Studies have shown that in plants transformed with ipt to overproduce cytokinins, the cytokinins work only locally as aparacrine hormone (Faiss et al., 1997). One problem with the use of ipt as a marker is that the resulting transgenic plants lose apical dominance and are unable to root due to overproduction of cytokinins (Ebinuma et al., 1 997).

Ebinuma et al. (1997) developed one method to use the ipt marker and to overcome the problems noted above. They developed a vector in which the ipt gene was inserted into a plasmid which included the transposable element Ac. The construct included the T-DNA (portion of the Ti plasmid that is transferred to plant cells) and the 35S CaMV promoter. This construct was transformed into *A. tumefaciens*. Leaf segments were inoculated with the transformed bacteria and grown on nonselective media. Abnormal shoots with an extra shooty phenotype were selected and cultivated further for six months. From these, several normal shoots grew. Some of these were a result of the transposable element Ac having excised.from the genome along with the ipt gene. This was determined by DNA analysis. Some of these few plants retained the other necessary markers which had also been included in the plasmid. This method therefore overcomes the problems of having a constitutively expressed ipt gene present. Unfortunately, this method requires many months of cultivation and results in only a few plants which have lost the ipt gene. Ebinuma et al. (1997) report that 6 months after infection the frequency of marker free plants was 0.032%.

The gene CKI1 was more recently identified (Kakimoto, 1996). Overproduction of this gene in plants results in plants which exhibit typical cytokinin responses, including rapid cell division and shoot formation in tissue culture in the absence of exogenous cytokinin (Kakimoto, 1996). The CKI1 gene can be used as a selectable marker in a manner similar to ipt, i.e., the CKI1 gene can be put under the control of a promoter and overexpressed in transgenic plant cells thereby inducing shoot formation in the absence of exogenous plant hormones. Such shoots can be excised thereby obtaining transgenic plants. Such shoots, obtained either from cells transformed with ipt or CKI1, cannot be made to grow normally while the cells are expressing these transgenes. The knotted gene and knotted-like genes are a third group of genes which when overexpressed can lead to ectopic production of adventitious shoots (Chuck et al., 1996; Lincoln et al., 1994). These can be used as selectable markers in the same manner as the ipt and CKI1 genes.

Besides the use of markers to identify transgenic plants, the use of promoters to control the transgenes is a normal part of such experiments. In most experiments, the transgenes are transcribed from a strong promoter, such as the 35S promoter of the cauliflower mosaic virus (CaMV). However, a more flexible gene expression system is needed to extract greater benefits from transgenic technology. Good inducible transcription systems are desired because transgenic plants with inducible phenotypes are as useful as conditional mutants isolated by traditional genetics. In this regard, several induction systems have been reported and successfully used (Ainley and Key, 1990; Gatz et al., 1992; Mett et al., 1993; Weinmann et al., 1994). Among these, the tetracycline-dependent expression systems are the most commonly used (for review, see Gatz, 1996). See Zuo and Chua (2000) for a review of chemical-inducible systems for regulated expression of plant genes.

The glucocorticoid receptor (GR) is a member of the family of vertebrate steroid hormone receptors. GR is not only a receptor molecule but also a transcription factor which, in the presence of a glucocorticoid, activates transcription from promoters containing glucocorticoid response elements (GREs) (for reviews, see Beato, 1989; Picard, 1993). It had been considered that the GR system could be a good induction system in plants because it is simple, and glucocorticoid itself does not cause any pleiotropic effects in plants. Schena et al. (1991) demonstrated that a system comprising GR and GREs could work in a transient expression system with cultured plant cells. It had been reported that the hormone-binding domain (HBD) of GR could regulate the function of plant transcription factors in transgenic plants (Aoyama et al., 1995; Lloyd et al., 1994). Aoyama and Chua (1997) then demonstrated a general and efficient glucocorticoid-inducible system using GR.

Despite the availability of the markers described above and the systems available for controlling the expression of the markers, the need for improved marker genes still exists. Furthermore, a need exists for improving the efficiency of organogenesis or regeneration of plant cells. The present invention addresses both of these needs.

The publications and other materials used herein to illuminate the background of the invention, and in particular cases to provide additional details respecting the practice, are incorporated herein by reference, and for convenience, are referenced by author and date in the text and respectively grouped in the appended List of References.

SUMMARY OF THE INVENTION

In one aspect, the invention relates to a gene which is useful as a selectable marker in transgenic plants. This gene is herein named Enhancer of Shoot Regeneration (Esr1). The encoded protein, ESR1, contains an AP2 domain which is found in various transcriptional factors of plants.

In a second aspect, the invention is drawn to a protein (ESR1) encoded by Esr1.

A third aspect of the invention is a method of using ESR1 as a selectable marker. Overexpression of ESR1 in plants or plant cells results in plants or cells which show cytokinin-independent growth. This allows the gene to be used as a selective marker by growing cells transformed with the gene in cytokinin-free medium.

In a fourth aspect of the invention, overexpression of ESR1 in plant cells grown in the presence of cytokinins results in extremely high regeneration efficiency. This aspect of the invention uses the gene not as a marker but as a means to increase the regeneration efficiency of plant cells.

DETAILED DESCRIPTION OF THE INVENTION

The present invention relates to transgenic plants which include the gene Esr1 (enhancer of shoot regeneration 1). This gene is shown as SEQ ID NO: 6 and is nearly identical with a gene reported in GenBank (Accession Number AC007357, gene F3F19.1 consisting of bases 2481–3467 of the GenBank sequence which is shown herein as SEQ ID NO: 10). The GenBank sequence differs from the Esr1 gene at four bases and the encoded proteins differ at a single amino acid residue. ESR1 is shown as SEQ ID NO: 7 and the GenBank encoded protein is shown as SEQ ID NO: 11. Overexpression of Esr1 allows cytokinin-independent growth of the plants or cells which are overexpressing the gene thereby allowing the gene to be used as a marker. Furthermore, overexpression of the gene in cells grown in the presence of cytokinins results in a high regeneration efficiency, thus allowing the gene to be used in a manner which increases plant regeneration.

Expression of Esr1 can be placed under the control of an inducible promoter. An inducible promoter can be one which can be turned on (induced) to select for cells or plants which have become transgenic but which will not be turned on under natural growth conditions. In this manner the selectable marker gene, although present in the transgenic plants, will be completely silent during the normal growth of the plants and should not interfere with the growth of the plants. Such a silent marker gene may also be more environmentally acceptable than, e.g., having an antibiotic resistance gene marker present wherein said resistance gene is expressed during the normal growth of the plant.

To use ESR1 as a silent marker, Esr1 can be placed in a vector with an inducible promoter and plant cells are then transformed with the vector. The plant cells are grown in the presence of an inducer to turn on expression of ESR1 but in media lacking cytokinins. The absence of cytokinins prevents the growth of nontransformed cells, but cells transformed with the vector will grow despite the lack of cytokinins in the medium because of overexpression of the ESR1 gene. Shoots or calli which grow can be selected and tested to ascertain that they do include the vector. Once transformed shoots or calli are selected, they can be grown under normal conditions in the absence of inducer thereby preventing expression of the ESR1 gene within the vector.

The vector which expresses Esr1 under the control of an inducible promoter can, if desired, include a second gene which will be expressed. This second gene can be under the control of an inducible promoter which is different from that controlling the ESR1 gene or it can be under the control of a constitutive promoter. This second gene can then be induced or produced constitutively in the transformed plants which are grown under normal conditions. The second gene can be any gene desired and can produce a protein which results in a more desirable trait than found in the nontransformed plant. Alternatively, plants can be cotransformed with one vector encoding ESR1 and with a second vector encoding the gene of interest. As the two transgenes will segregate in subsequent transgenic generations, transgenic plants carrying only the gene of interest can be obtained this way.

One inducible promoter under which the Esr1 gene can be placed is the glucocorticoid receptor (Aoyama and Chua, 1997). This has been considered to be a good induction system for plants because glucocorticoid itself does not cause any apparent pleiotropic effects in plants. The use of a steroid receptor domain to regulate gene expression in transgenic plants has been previously reported by Lloyd et al. (1994), who showed that trichome development in *Arabidopsis* could be successfully controlled by a chimeric protein comprising the glucocorticoid receptor domain and the maize transcriptional regulator R. Tight transcriptional regulation with these systems appears to be dependent on the intramolecular structure of the chimeric protein, especially the relative position between the glucocorticoid receptor domain and the domain whose function is to be regulated. Although the glucocorticoid receptor-regulated promoter is a useful one which can be used together with ESR1, Esr1 can be used together with any inducible promoter which is desired. For a recent review of chemical-inducible systems for regulated expression of plant genes see Zuo and Chua (2000).

In addition to its use as a marker, especially as a silent marker, overexpression of Esr1 in the presence of cytokinins results in enhanced regeneration efficiency. This result allows one several options for increasing yields of transformed plants. Vectors can be prepared which contain both a gene of interest as well as Esr1. Plant cells are then transformed with these vectors and the cells are cultured. In a first method, the cells can first be cultured on media lacking cytokinins but including an inducer of the ESR1 gene and the shoots and calli which grow can be selected and then grown normally. In a second method, the cells can be grown on media with cytokinins and with an inducer of Esr1 This second method allows greater regeneration efficiency thereby resulting in more shoot or callus formation. If desired, this second method can be performed with a vector comprising yet a third gene which can encode a selectable marker, e.g., an antibiotic resistance gene. In this method, a vector comprising Esr1 under the control of an inducible promoter, the antibiotic resistance marker gene, and the gene of interest is used to transform cells. The cells are then grown on a medium with an inducer of Esr1, an antibiotic, and cytokinins. The expression of Esr1 results in enhanced regeneration efficiency while the antibiotic resistance gene acts as a selectable marker. The gene of interest will be present in the selected shoots.

The vectors to be used in forming transgenic plants can include a chemically inducible promoter such as the glucocorticoid promoter which will activate the selectable marker but can include any other desired promoter in place of or in addition to the GR system promoter. If desired, any other gene of interest can also be put under control of the inducible promoter such that the gene could be turned on whenever desired. Such a gene need not be a marker.

The present invention is described by reference to the following Examples, which are offered by way of illustration and are not intended to limit the invention in any manner. Standard techniques well known in the art or the techniques specifically described below were utilized.

EXAMPLE 1

Construction of a cDNA Library

Poly A RNAs were prepared using the Straight A's MRNA Isolation System (Novagen) using as source material a mixture of 7-day old seedlings, mature plant before flowering, root culture tissue, root culture tissue (all plants and plant tissue used were *Arabidopsis thaliana Wassilewskija*) treated with 0.15 mg/L indole acetic acid (IAA) and 5.0 mg/L of benzyladenine (BA) for 1 day, root culture tissue treated with IAA and BA as above except for 3 days, and root culture tissue treated with IAA and BA as above except for 5 days. Double stranded cDNAs were synthesized, using the SMART™ cDNA Technology from Clontech, from 1 mg of the prepared poly A RNAs using Anchor oligo dT primer 5'-AAGCAGTGGTAACAACGCAGAGT GCGGCCGCTTTTTTTTTTTTTTTTTA/G/C-3' (SEQ ID NO: 1) (a mixture of nucleic acids ending in A, G or C) and using a second strand primer of 5'-AAGCAGTGGTAACAACGCAGA GTGGCGCGCCGGG-3' (SEQ ID NO: 2) and using SuperScriptII RNase H$^-$ Reverse Transcriptase (Gibco BRL) and the buffer provided by the manufacturer (Gibco BRL).

The resulting cDNAs were treated with RNAse A (1 μg/mL) at 37° C. for 15 minutes and gel filtered on Microspin S-400 (Pharmacia) and then were amplified by a polymerase chain reaction (PCR) using the primer 5'-AAGCAGTGGTAACAACGCAGAGTG-3' (SEQ ID NO: 3). PCR was eight cycles (95° C. for 20 seconds, 65° C. for 30 seconds, 72° C. for 6 minutes) using Takara LA Taq and the buffer provided by the manufacturer (Panvera). One third of the amplified cDNAs were digested with AscI and NotI and then ligated to the plasmid pZL2 which is a-derivative of pZL1 (Gibco BRL). pZL2 was prepared by changing the SmaI site of pZL1 to an AscI site by ligating an AscI linker (GGCGCGCC) after digestion of pZL1 with SmaI. The ligated DNAs were transformed into *E. coli* DH10B (Gibco BRL). Plasmid DNAs from the transformants were used as templates for PCR.

EXAMPLE 2

Normalization of the cDNAs

Normalization of cDNAs was performed by self-subtraction. cDNAs obtained from abundant RNAs hybridize with their complements more efficiently than do cDNAs obtained from less abundant RNAs. Using biotinylated driver cDNAs, double stranded DNAs are removed by avidin after hybridization. This decreases the concentration of cDNA encoding abundant RNAs by a self-subtraction procedure.

Biotin-labeled driver DNAs were synthesized by PCR. 0.1 μg of the plasmid DNAs for the templates of PCR, T7 primer 5'-AGCTCTAATACGACTCACTATAGGG-3' (SEQ ID NO: 4) and SP6 primer 5'-AATTGAATTTAGGTGACACTATAGAAG-3' (SEQ ID NO: 5) were used for the PCR. The reaction mixture contained 0.2 mM of dATP, dGTP, dCTP and 0.15 mM of dTTP and 0.05 mM of Biotin-16-dUTP (Boehringer). To prevent hybridization between primer sequences, the driver DNAs were digested with AscI and NotI then gel-filtered using a Sephacryl S-300 spun column (Pharmacia). 50 ng of the tracer DNAs (cDNAs synthesized by PCR in Example 1) and 5 μg of the driver DNAs (the biotin-labeled DNAs above) were hybridized in 50 μL of QuickHyb (Clontech) adjusted to pH 9.3 at 68° C. for 4 hours. The reaction mixture was incubated with 100 μL of streptavidin magnetic particles (Boehringer) at room temperature for 10 minutes and the particles were removed using a Magnetic Stand (Promega). This procedure was repeated three times. The final supernatant was precipitated with ethanol and amplified by five cycles of PCR using SEQ ID NO: 3 as primer. 0.1 μg of the amplified cDNAs was again hybridized with the driver DNA above and subtracted by the same procedure. The subtracted cDNAs were amplified by eight cycles of PCR using SEQ ID NO: 3 as a primer and then digested with AscI and NotI. The digested cDNAs were cloned between a Cauliflower Mosaic Virus 35S promoter and a nopaline synthetase terminator in plasmid pSK34 (a derivative of pSK1 (Kojima et al., 1999)) digested with AscI and NotI. pSK34 was constructed by replacing the 35S promoter-hygromycin phosphotransferase-Nos terminator cassette by Nos promoter-neomycin phosphotransferase II-Nos terminator cassette and the multiple cloning sites were changed by ligating a linker (5'-CTAGAGGCGCGCCACCGGTGC-3' (SEQ ID NO: 8) (top strand) and 5'-GGCCGCACCGGTGGCGCGCCT-3' (SEQ ID NO: 9) (bottom strand)) after digestion with XbaI and NotI. The plasmid cDNA library was amplified once in *E. coli* DH10 B and then transformed into Agrobacterium EHA 105.

EXAMPLE 3

Screening of Shoots which Can Grow without Cytokinin

Seven-day old *Arabidopsis thaliana ecotype* WS seedlings were transferred into Gamborg B5 medium (Life Technologies) and cultured with shaking at 125 rpm for two weeks at 22° C. under constant illumination. Roots of the culture were cut into approximately 5 mm and transferred onto plates containing Gamborg B5 medium (Life Technologies) supplemented with 0.5 mg/L of 2,4-dichlorophenoxy acetic acid, 0.05 mg/L of kinetin (F medium) and 0.6% Phytagel™ (Sigma) for 3 days. The root culture was mixed with *Agrobacterium* carrying the normalized cDNA library from Example 2 in F medium. The root culture was then transferred onto F plates supplemented with 50 μg/L of acetosyringone and 0.6% of Phytagel™ and incubated for 3 days. The root culture was washed with sterile water five times and suspended in C medium (Murashige and Skoog Salt Base (JRH Biosciences) supplemented with 1% sucrose, 0.15 mg/L of IAA, 400 mg/L of carbenicillin and 50 mg/L of kanamycin) containing 0.5% low melting temperature agarose, then spread on C medium containing 0.25% Phytagel™. The plates were incubated for six weeks under continuous light. Potential populations of $1\times10^5$ independent transformed shoots were screened, as estimated from parallel experiments in which 1/100 of transformed root culture was incubated on plates with cytokinin. As a result of the screening, nine shoots and one dark green callus were formed.

EXAMPLE 4

Retransformation

A cDNA insert was recovered by PCR from the dark green callus obtained in Example 3. Plant DNAs were prepared from transgenic *Arabidopsis* tissues using a DNAeasy plant mini kit (Qiagen). Plant DNA (50 ng) was used for templates. PCR was performed by 35 cycles (95° C. for 20 sec, 58° C. for 30 sec, 72° C. for 6 min) using Takara LA Taq, supplemented buffer with Takara LA Taq, 35 SEV primer (5'-GATATCTCCACTGACGTAAGG-3' (SEQ ID NO: 12)) and NOS1 primer (5'-AACGATCGGGGAAATTCGAGCTGCGG-3' (SEQ ID NO: 13)). The cDNA was cloned into the plasmid pSK34 under the control of a 35S promoter and transformed into *Agrobacterium* EHA 105. The cDNA was named Enhancer for Shoot Regeneration 1 (Esr1). The sequence of the Esr1 cDNA is shown as SEQ ID NO: 6 and the encoded protein is SEQ ID NO: 7.

*Arabidopsis* roots were retransformed with 35S-Esr1 cDNA in pSK34 and cultured. About 15 shoots and/or green calli were obtained per C plate (0.1 gram of roots). The number of regenerants was comparable to the number obtained when roots were transformed by *Agrobacterium* EHA105 containing the pSK34 vector alone. In this case the regenerants were selected on C media supplemented with cytokinin. Transformation with pSK34 alone followed by incubation in C medium without added cytokinin did not result in any regeneration of shoots.

EXAMPLE 5

Effects of Esr1 Overexpression on Root Transformation

Esr1 was cloned into the XVE vector pER10 (see U.S. patent application Ser. No. 09/439,535, filed Nov. 12, 1999, which is incorporated herein by reference) for inducible expression. pER-Esr1 was constructed by inserting a 1.3 kbp fragment of ESR1 cDNA (prepared by digesting with NotI and blunt ending with Klenow, then digesting with Ascl) into pER 10 which had been digested with SpeI and blunt ended with Klenow, then digested with AscI. The expression of Esr1 cDNA is induced by 17β-estradiol under the control of the strong XVE transcription factor. *Arabidopsis* root cultures were transformed with pER10 or pER-Esr1 as described in Example 3 and then transferred onto C plates with or without an inducer, or C plates with cytokinin with or without an inducer. The number of shoots generated on plates were scored after 4 weeks. 5 mg/L of 2-isopentenyl adenine was added for cytokinin and 10 μM 17β-estradiol was used as an inducer of expression. Results are shown in Table 1. The values were calculated to show the number of shoot regenerants obtained from 1 g of fresh root culture.

TABLE 1

| | Number of Shoots Generated | |
|---|---|---|
| Treatment | pER10 | pER-ESR1 |
| −cytokinin, −inducer | 0 | 0 |
| −cytokinin, +inducer | 0 | 129 |
| +cytokinin, −inducer | 149 | 132 |
| +cytokinin, +inducer | 142 | 2476 |

Overexpression of Esr1 (with an inducer) in the absence of cytokinin gave a similar number of shoots as the vector alone in the presence of cytokinin, which may explain the identification of Esr1 by the screening in Example 3. Surprisingly, overexpression of ESR1 (with an inducer) gave 16–18 fold higher number of shoots in the presence of cytokinin compared with the vector alone in the presence of cytokinin, or compared with pER-ESR1 without an inducer in the presence of cytokinin. These results demonstrated that overexpression of Esr1 can be used for efficient production of transgenic plants.

Plants or plant cells containing the pER-Esr1 vector can be co-transformed with pER-Esr1 and a second vector with a desired gene. Such plants can be efficiently generated when grown in the presence of cytokinin and in inducer for the XVE promoter. Transgenic plants carrying only the gene of interest can be recovered in subsequent generations after segregation of the transgenes. It is also possible to insert a gene of interest into the same vector which comprises Esr1 and to use this vector to transform plants or plant cells, thereby resulting in a plant or plant cell containing only a single vector and which can be efficiently regenerated and comprised a vector with the gene of interest. Sse83871 site can be available as a unique site for inserting an expression cassette containing a promoter, a gene of interest and a terminator.

EXAMPLE 6

Use of ESR1 as a Marker for Transformation pER-Esr1 gave a comparable number of shoots in the absence of cytokinin as that of the vector alone in the presence of cytokinin (when the regenerants are selected by resistance to the antibiotic marker) or that of pER-Esr1 without an inducer in the presence of cytokinin (when the regenerants are selected by resistance to the antibiotic marker) while no shoots were generated without cytokinin when transformed with the vector alone. These results demonstrated that overexpression of Esr1 can be used as a selectable marker method.

While the invention has been disclosed herein by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

References

Ainley W M and Key J L (1990). *Plant Mol. Biol.* 14:949–966.

Aoyama T and Chua N-H (1997). *The Plant J*. 11:605–612.

Aoyama T, Dong C-H, Wu Y, Carabelli M, Sessa G, Ruberti I, Morelli G and Chua N-H (1995). *Plant Cell* 7:1773–1785.

Barry G F, Rogers S G, Fraley R T and Brand L (1984). *Proc. Natl. Acad. Sci. USA* 81:4776–4780.

Beato M (1989). *Cell* 56:335–344.

Bryant J and Leather S (1992). *Trends Biotechnol.* 10:274–275.

Chuck G, Lincoln C and Hake S (1996). *The Plant Cell* 8:1277–1289.

Ebinuma H, Sugita K, Matsunaga E and Yamakado M (1997). *Proc. Natl. Acad. Sci. USA* 94:2117–2121.

Faiss M, Zalubilova J, Strnad M and Schmutlling T (1997). *The Plant Journal* 12:401–415.

Flavell R B, Dart E, Fuchs R L and Fraley R B (1992). *Bio/Technology* 10: 141–144.

Gatz C (1996). Curr. Opin. *Biotechnol.* 7:168–172.

Gatz C, Frohberg C and Wendenburg R (1992). *Plant J*. 2:397–404.

Gressel J (1992). *Trends Biotechnol.* 10:382.

Kakimoto T (1996). *Science* 274:982–985.

Kojima S, Banno H, Yoshioka Y, Oka A, Machida C and Machida Y (1999). *DNA Res*. 6:407–410.

Lincoln C, Long J, Yamaguchi J, Serikawa K and Hake S (1994). *The Plant Cell* 6:1859–1876.

Lloyd A M, Schena M, Walbot V and Davis R W (1994). *Science* 266:436–439.

Mett V L, Lockhead L P and Reynolds PHS (1993). *Proc. Natl. Acad. Sci. USA* 90:4567–4571.

Ooms G, Kaup A and Roberts J (1983). *Theor. Appl. Genet*. 66:169–172.

Picard D (1993). *Trends Cell Biol*. 3:278–280.

Riou-Khamlichi C, Huntley R, Jacqmard A and Murray J A (1999). *Science* 283:1541–1544.

Schena M, Lloyd A M and Davis R W (1991). *Proc. Natl. Acad. Sci. USA* 88:10421–10425.

Smigocki A C and Owens L D (1988). *Proc. Natl. Acad. Sci. USA* 85:5131–5135.

Smigocki A C and Owens L D (1989). *Plant Physiol.* 91:808–811.

Weinmann P, Gossen M, Hillen W, Bujard H and Gatz C (1994). *Plant J*. 5:559–569.

Yoder J I and Goldsbrough A P (1994). *Bio/Technology* 12:263–267.

Zuo J and Chua N-H (2000). *Current Opinion in Biotechnology* 11:146–151.

What is claimed is:

1. A method for increasing regeneration efficiency of transformed plant cells comprising:

(a) transforming plant cells with a vector comprising a nucleic acid encoding a protein of SEQ ID NO:7 or of SEQ ID NO:11 to produce transformed plant cells; and (b) culturing said transformed plant cells to produce transformed plants under conditions wherein said protein is expressed in the presence of added cytokinin;

wherein regeneration of transformed plants produced in step (b) occurs at a higher rate than does regeneration of plants from non-transformed plant cells.

2. The method of claim 1 wherein said nucleic acid is under the control of an inducible promoter and wherein step (b) is performed in the presence of an inducer of said inducible promoter.

3. The method of claim 1 wherein said vector further comprises a nucleic acid of interest.

4. A method for increasing regeneration efficiency of transformed plant cells comprising:

(a) transforming plant cells with a vector comprising a nucleic acid of interest wherein said plant cells were previously transformed with a vector comprising a nucleic acid encoding a protein of SEQ ID NO:7 or of SEQ ID NO:11;

(b) culturing said transformed plant cells to produce transformed plants under conditions wherein said protein is expressed in the presence of added cytokinin;

wherein regeneration of transformed plants produced in step (b) occurs at a higher rate than does regeneration of plants from non-transformed plant cell.

5. The method of claim 4 wherein said protein encoding nucleic acid is under the control of an inducible promoter and wherein step (b) is performed in the presence of an inducer of said inducible promoter.

* * * * *

SEQUENCE LISTING

```
<160> NUMBER OF SEQ ID NOS: 13

<210> SEQ ID NO 1
<211> LENGTH: 48
<212> TYPE: DNA
<213> ORGANISM: Artificial Sequence
<220> FEATURE:
<223> OTHER INFORMATION: Description of Artificial Sequence:Oligo dT
      primer.

<400> SEQUENCE: 1

aagcagtggt aacaacgcag agtgcggccg cttttttttt tttttttv              48


<210> SEQ ID NO 2
<211> LENGTH: 34
<212> TYPE: DNA
<213> ORGANISM: Artificial Sequence
<220> FEATURE:
<223> OTHER INFORMATION: Description of Artificial Sequence:Second
      strand synthesis primer.

<400> SEQUENCE: 2

aagcagtggt aacaacgcag agtggcgcgc cggg                             34


<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:PCR primer.

<400> SEQUENCE: 3

aagcagtggt aacaacgcag agtg                                        24


<210> SEQ ID NO 4
```

-continued

```
<211> LENGTH: 25
<212> TYPE: DNA
<213> ORGANISM: Artificial Sequence
<220> FEATURE:
<223> OTHER INFORMATION: Description of Artificial Sequence:T7 primer.

<400> SEQUENCE: 4

agctctaata cgactcacta taggg                                          25


<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence:SP6 primer.

<400> SEQUENCE: 5

aattgaattt aggtgacact atagaag                                        27


<210> SEQ ID NO 6
<211> LENGTH: 1265
<212> TYPE: DNA
<213> ORGANISM: Arabidopsis thaliana
<220> FEATURE:
<221> NAME/KEY: CDS
<222> LOCATION: (76)..(1059)

<400> SEQUENCE: 6

ggaaactatc aaccaccaaa atctttcaca ttacaccttc cttttgtcct caaaccaaaa     60

ccctagaaac caaaa atg gaa aaa gcc ttg aga aac ttc acc gaa tct acc     111
                 Met Glu Lys Ala Leu Arg Asn Phe Thr Glu Ser Thr
                   1               5                  10

cac tca cca gac cct aat cct ctc aca aaa ttc ttc act gaa cct aca      159
His Ser Pro Asp Pro Asn Pro Leu Thr Lys Phe Phe Thr Glu Pro Thr
         15                  20                  25

gcc tca cct gtt agc cgc aac cgc aaa ctg tct tca aaa gat acc act      207
Ala Ser Pro Val Ser Arg Asn Arg Lys Leu Ser Ser Lys Asp Thr Thr
     30                  35                  40

gta acc atc gcc gga gct ggc agc agc acg acg agg tac cgc ggc gta      255
Val Thr Ile Ala Gly Ala Gly Ser Ser Thr Thr Arg Tyr Arg Gly Val
 45                  50                  55                  60

cgc cgg agg ccg tgg gga cga tac gcg gcg gag ata cgt gac cca atg      303
Arg Arg Arg Pro Trp Gly Arg Tyr Ala Ala Glu Ile Arg Asp Pro Met
                 65                  70                  75

tcg aag gag aga cgt tgg ctc gga aca ttt gac acg gcg gaa caa gcc      351
Ser Lys Glu Arg Arg Trp Leu Gly Thr Phe Asp Thr Ala Glu Gln Ala
             80                  85                  90

gct tgt gct tac gac tct gcg gct cgt gcc ttt cgt gga gca aag gct      399
Ala Cys Ala Tyr Asp Ser Ala Ala Arg Ala Phe Arg Gly Ala Lys Ala
         95                 100                 105

cgt act aat ttt act tat ccg aca gct gtc att atg cct gaa cca agg      447
Arg Thr Asn Phe Thr Tyr Pro Thr Ala Val Ile Met Pro Glu Pro Arg
    110                 115                 120

ttt tct ttt tcc aac aag aaa tct tcg ccg tct gct cgt tgt cct ctt      495
Phe Ser Phe Ser Asn Lys Lys Ser Ser Pro Ser Ala Arg Cys Pro Leu
125                 130                 135                 140

cct tct cta ccg tta gat tcc tct acc caa aac ttt tac ggt gca ccg      543
Pro Ser Leu Pro Leu Asp Ser Ser Thr Gln Asn Phe Tyr Gly Ala Pro
                145                 150                 155

gca gcg cag agg atc tat aat aca cag tct atc ttc tta cgc gac gcc      591
Ala Ala Gln Arg Ile Tyr Asn Thr Gln Ser Ile Phe Leu Arg Asp Ala
            160                 165                 170
```

-continued

```
tcg tgt tcc tct cgt aaa acg act ccc tat aat aac tct ttc aac ggc      639
Ser Cys Ser Ser Arg Lys Thr Thr Pro Tyr Asn Asn Ser Phe Asn Gly
        175                 180                 185

tca tca tct tct tac tca gca tcg aaa acg gca tgc gtt tct tat tcc      687
Ser Ser Ser Ser Tyr Ser Ala Ser Lys Thr Ala Cys Val Ser Tyr Ser
    190                 195                 200

gaa aac gaa aac aac gag tcg ttt ttc ccg gaa gaa tct tct gat act      735
Glu Asn Glu Asn Asn Glu Ser Phe Phe Pro Glu Glu Ser Ser Asp Thr
205                 210                 215                 220

ggt cta tta caa gag gtc gtt caa gag ttc ttg aag aaa aat cgc ggc      783
Gly Leu Leu Gln Glu Val Val Gln Glu Phe Leu Lys Lys Asn Arg Gly
                225                 230                 235

gtt cct cct tct cca cca aca cca ccg ccg gtg act agc cat cat gac      831
Val Pro Pro Ser Pro Pro Thr Pro Pro Pro Val Thr Ser His His Asp
            240                 245                 250

aac tct ggt tat ttc tct gct ctc act ata tac tct gaa aat atg gtt      879
Asn Ser Gly Tyr Phe Ser Ala Leu Thr Ile Tyr Ser Glu Asn Met Val
        255                 260                 265

caa gag act aag gag act ttg tcg tcg aaa cta gat cgc tac ggg aat      927
Gln Glu Thr Lys Glu Thr Leu Ser Ser Lys Leu Asp Arg Tyr Gly Asn
    270                 275                 280

ttt caa gct aat gac gac ggc gta aga gcc gtc gca gac ggt ggt tta      975
Phe Gln Ala Asn Asp Asp Gly Val Arg Ala Val Ala Asp Gly Gly Leu
285                 290                 295                 300

tct ttg gga tca aac gag tgg ggg tat caa gaa atg ttg atg tac gga     1023
Ser Leu Gly Ser Asn Glu Trp Gly Tyr Gln Glu Met Leu Met Tyr Gly
                305                 310                 315

act cag tta ggc tgt act tgc cga aga tcg tgg gga tagctagata          1069
Thr Gln Leu Gly Cys Thr Cys Arg Arg Ser Trp Gly
            320                 325

ttcatcatga ttatgttttg agttttggta ctatcgactt agtttaaagt tgctaccttt   1129

cccaatgttg gatattaact aaattatgtt ttaagttgaa tttgctaata ggatttcata   1189

attataatca agtttataat atattttagt agctaattaa agtttatatc cacgtattct   1249

gaaaaaaaaa aaaaaa                                                   1265


<210> SEQ ID NO 7
<211> LENGTH: 328
<212> TYPE: PRT
<213> ORGANISM: Arabidopsis thaliana

<400> SEQUENCE: 7

Met Glu Lys Ala Leu Arg Asn Phe Thr Glu Ser Thr His Ser Pro Asp
  1               5                  10                  15

Pro Asn Pro Leu Thr Lys Phe Phe Thr Glu Pro Thr Ala Ser Pro Val
             20                  25                  30

Ser Arg Asn Arg Lys Leu Ser Ser Lys Asp Thr Thr Val Thr Ile Ala
         35                  40                  45

Gly Ala Gly Ser Ser Thr Thr Arg Tyr Arg Gly Val Arg Arg Arg Pro
     50                  55                  60

Trp Gly Arg Tyr Ala Ala Glu Ile Arg Asp Pro Met Ser Lys Glu Arg
 65                  70                  75                  80

Arg Trp Leu Gly Thr Phe Asp Thr Ala Glu Gln Ala Ala Cys Ala Tyr
                 85                  90                  95

Asp Ser Ala Ala Arg Ala Phe Arg Gly Ala Lys Ala Arg Thr Asn Phe
            100                 105                 110

Thr Tyr Pro Thr Ala Val Ile Met Pro Glu Pro Arg Phe Ser Phe Ser
        115                 120                 125
```

-continued

```
Asn Lys Lys Ser Ser Pro Ser Ala Arg Cys Pro Leu Pro Ser Leu Pro
    130                 135                 140

Leu Asp Ser Ser Thr Gln Asn Phe Tyr Gly Ala Pro Ala Ala Gln Arg
145                 150                 155                 160

Ile Tyr Asn Thr Gln Ser Ile Phe Leu Arg Asp Ala Ser Cys Ser Ser
                165                 170                 175

Arg Lys Thr Thr Pro Tyr Asn Asn Ser Phe Asn Gly Ser Ser Ser Ser
            180                 185                 190

Tyr Ser Ala Ser Lys Thr Ala Cys Val Ser Tyr Ser Glu Asn Glu Asn
        195                 200                 205

Asn Glu Ser Phe Phe Pro Glu Glu Ser Ser Asp Thr Gly Leu Leu Gln
    210                 215                 220

Glu Val Val Gln Glu Phe Leu Lys Lys Asn Arg Gly Val Pro Pro Ser
225                 230                 235                 240

Pro Pro Thr Pro Pro Pro Val Thr Ser His His Asp Asn Ser Gly Tyr
                245                 250                 255

Phe Ser Ala Leu Thr Ile Tyr Ser Glu Asn Met Val Gln Glu Thr Lys
            260                 265                 270

Glu Thr Leu Ser Ser Lys Leu Asp Arg Tyr Gly Asn Phe Gln Ala Asn
        275                 280                 285

Asp Asp Gly Val Arg Ala Val Ala Asp Gly Gly Leu Ser Leu Gly Ser
    290                 295                 300

Asn Glu Trp Gly Tyr Gln Glu Met Leu Met Tyr Gly Thr Gln Leu Gly
305                 310                 315                 320

Cys Thr Cys Arg Arg Ser Trp Gly
                325


<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:Top strand
      of linker.

<400> SEQUENCE: 8

ctagaggcgc gccaccggtg c                                              21


<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:Bottom
      strand of linker.

<400> SEQUENCE: 9

ggccgcaccg gtggcgcgcc t                                              21


<210> SEQ ID NO 10
<211> LENGTH: 987
<212> TYPE: DNA
<213> ORGANISM: Arabidopsis thaliana
<220> FEATURE:
<221> NAME/KEY: CDS
<222> LOCATION: (1)..(984)

<400> SEQUENCE: 10

atg gaa aaa gcc ttg aga aac ttc acc gaa tct acc cac tca cca gac      48
Met Glu Lys Ala Leu Arg Asn Phe Thr Glu Ser Thr His Ser Pro Asp
```

-continued

```
 1               5                  10                  15

cct aat cct ctc aca aaa ttc ttc act gaa cct aca gcc tca cct gtt       96
Pro Asn Pro Leu Thr Lys Phe Phe Thr Glu Pro Thr Ala Ser Pro Val
            20                  25                  30

agc cgc aac cgc aaa ctg tct tca aaa gat acc act gta acc atc gcc      144
Ser Arg Asn Arg Lys Leu Ser Ser Lys Asp Thr Thr Val Thr Ile Ala
        35                  40                  45

gga gct ggc agc agc acg acg agg tac cgc ggc gta cgc cgg agg ccg      192
Gly Ala Gly Ser Ser Thr Thr Arg Tyr Arg Gly Val Arg Arg Arg Pro
    50                  55                  60

tgg gga cga tac gcg gcg gag ata cgt gac cca atg tcg aag gag aga      240
Trp Gly Arg Tyr Ala Ala Glu Ile Arg Asp Pro Met Ser Lys Glu Arg
65                  70                  75                  80

cgt tgg ctc gga aca ttt gac acg gcg gaa caa gcc gct tgt gct tac      288
Arg Trp Leu Gly Thr Phe Asp Thr Ala Glu Gln Ala Ala Cys Ala Tyr
                85                  90                  95

gac tct gcg gct cgt gcc ttt cgt gga gca aag gct cgt act aat ttt      336
Asp Ser Ala Ala Arg Ala Phe Arg Gly Ala Lys Ala Arg Thr Asn Phe
            100                 105                 110

act tat ccg aca gct gtc att atg cct gaa cca agg ttt tct ttt tcc      384
Thr Tyr Pro Thr Ala Val Ile Met Pro Glu Pro Arg Phe Ser Phe Ser
        115                 120                 125

aac aag aaa tct tcg ccg tct gct cgt tgt cct ctt cct tct cta ccg      432
Asn Lys Lys Ser Ser Pro Ser Ala Arg Cys Pro Leu Pro Ser Leu Pro
    130                 135                 140

tta gat tcc tct acc caa aac ttt tac ggt gca ccg gca gcg cag agg      480
Leu Asp Ser Ser Thr Gln Asn Phe Tyr Gly Ala Pro Ala Ala Gln Arg
145                 150                 155                 160

atc tat aat aca cag tct atc ttc tta cgc gac gcc tcg tgt tcc tct      528
Ile Tyr Asn Thr Gln Ser Ile Phe Leu Arg Asp Ala Ser Cys Ser Ser
                165                 170                 175

cgt aaa acg act ccg tat aat aac tct ttc aac ggc tca tca tct tct      576
Arg Lys Thr Thr Pro Tyr Asn Asn Ser Phe Asn Gly Ser Ser Ser Ser
            180                 185                 190

tac tca gca tcg aaa acg gca tgc gtt tct tat tcc gaa aac gaa aac      624
Tyr Ser Ala Ser Lys Thr Ala Cys Val Ser Tyr Ser Glu Asn Glu Asn
        195                 200                 205

aac gag tcg ttt ttc ccg gaa gaa tct tct gat act ggt cta tta caa      672
Asn Glu Ser Phe Phe Pro Glu Glu Ser Ser Asp Thr Gly Leu Leu Gln
    210                 215                 220

gag gtc gtt caa gag ttc ttg aag aaa aat cgc ggc gtt cct cct tct      720
Glu Val Val Gln Glu Phe Leu Lys Lys Asn Arg Gly Val Pro Pro Ser
225                 230                 235                 240

cca cca aca cca ccg ccg gtg act agc cat cat gac aac tct ggt tat      768
Pro Pro Thr Pro Pro Pro Val Thr Ser His His Asp Asn Ser Gly Tyr
                245                 250                 255

ttc tct aat ctc act ata tac tct gaa aat atg gtt caa gag act aag      816
Phe Ser Asn Leu Thr Ile Tyr Ser Glu Asn Met Val Gln Glu Thr Lys
            260                 265                 270

gag act ttg tcg tcg aaa cta gat cgc tac ggg aat ttt caa gct aat      864
Glu Thr Leu Ser Ser Lys Leu Asp Arg Tyr Gly Asn Phe Gln Ala Asn
        275                 280                 285

gac gac ggc gta aga gcc gtc gca gac ggt ggt tta tcg ttg gga tca      912
Asp Asp Gly Val Arg Ala Val Ala Asp Gly Gly Leu Ser Leu Gly Ser
    290                 295                 300

aac gag tgg ggg tat caa gaa atg ttg atg tac gga act cag tta ggc      960
Asn Glu Trp Gly Tyr Gln Glu Met Leu Met Tyr Gly Thr Gln Leu Gly
305                 310                 315                 320

tgt act tgc cga aga tcg tgg gga tag                                  987
```

-continued

```
Cys Thr Cys Arg Arg Ser Trp Gly
                325


<210> SEQ ID NO 11
<211> LENGTH: 328
<212> TYPE: PRT
<213> ORGANISM: Arabidopsis thaliana

<400> SEQUENCE: 11

Met Glu Lys Ala Leu Arg Asn Phe Thr Glu Ser Thr His Ser Pro Asp
  1               5                  10                  15

Pro Asn Pro Leu Thr Lys Phe Phe Thr Glu Pro Thr Ala Ser Pro Val
             20                  25                  30

Ser Arg Asn Arg Lys Leu Ser Ser Lys Asp Thr Thr Val Thr Ile Ala
         35                  40                  45

Gly Ala Gly Ser Ser Thr Thr Arg Tyr Arg Gly Val Arg Arg Arg Pro
     50                  55                  60

Trp Gly Arg Tyr Ala Ala Glu Ile Arg Asp Pro Met Ser Lys Glu Arg
 65                  70                  75                  80

Arg Trp Leu Gly Thr Phe Asp Thr Ala Glu Gln Ala Ala Cys Ala Tyr
                 85                  90                  95

Asp Ser Ala Ala Arg Ala Phe Arg Gly Ala Lys Ala Arg Thr Asn Phe
            100                 105                 110

Thr Tyr Pro Thr Ala Val Ile Met Pro Glu Pro Arg Phe Ser Phe Ser
        115                 120                 125

Asn Lys Lys Ser Ser Pro Ser Ala Arg Cys Pro Leu Pro Ser Leu Pro
    130                 135                 140

Leu Asp Ser Ser Thr Gln Asn Phe Tyr Gly Ala Pro Ala Ala Gln Arg
145                 150                 155                 160

Ile Tyr Asn Thr Gln Ser Ile Phe Leu Arg Asp Ala Ser Cys Ser Ser
                165                 170                 175

Arg Lys Thr Thr Pro Tyr Asn Asn Ser Phe Asn Gly Ser Ser Ser Ser
            180                 185                 190

Tyr Ser Ala Ser Lys Thr Ala Cys Val Ser Tyr Ser Glu Asn Glu Asn
        195                 200                 205

Asn Glu Ser Phe Phe Pro Glu Glu Ser Ser Asp Thr Gly Leu Leu Gln
    210                 215                 220

Glu Val Val Gln Glu Phe Leu Lys Lys Asn Arg Gly Val Pro Pro Ser
225                 230                 235                 240

Pro Pro Thr Pro Pro Pro Val Thr Ser His His Asp Asn Ser Gly Tyr
                245                 250                 255

Phe Ser Asn Leu Thr Ile Tyr Ser Glu Asn Met Val Gln Glu Thr Lys
            260                 265                 270

Glu Thr Leu Ser Ser Lys Leu Asp Arg Tyr Gly Asn Phe Gln Ala Asn
        275                 280                 285

Asp Asp Gly Val Arg Ala Val Ala Asp Gly Gly Leu Ser Leu Gly Ser
    290                 295                 300

Asn Glu Trp Gly Tyr Gln Glu Met Leu Met Tyr Gly Thr Gln Leu Gly
305                 310                 315                 320

Cys Thr Cys Arg Arg Ser Trp Gly
                325


<210> SEQ ID NO 12
<211> LENGTH: 21
<212> TYPE: DNA
<213> ORGANISM: Artificial Sequence
```

-continued

```
<220> FEATURE:
<223> OTHER INFORMATION: Description of Artificial Sequence:35 SEV
      primer.

<400> SEQUENCE: 12

gatatctcca ctgacgtaag g                                           21


<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence:NOS1 primer.

<400> SEQUENCE: 13

aacgatcggg gaaattcgag ctgcgg                                      26
```